Aug. 15, 1950 J. DE VINK Plant Pat. 973
ROSE PLANT
Filed Aug. 5, 1949
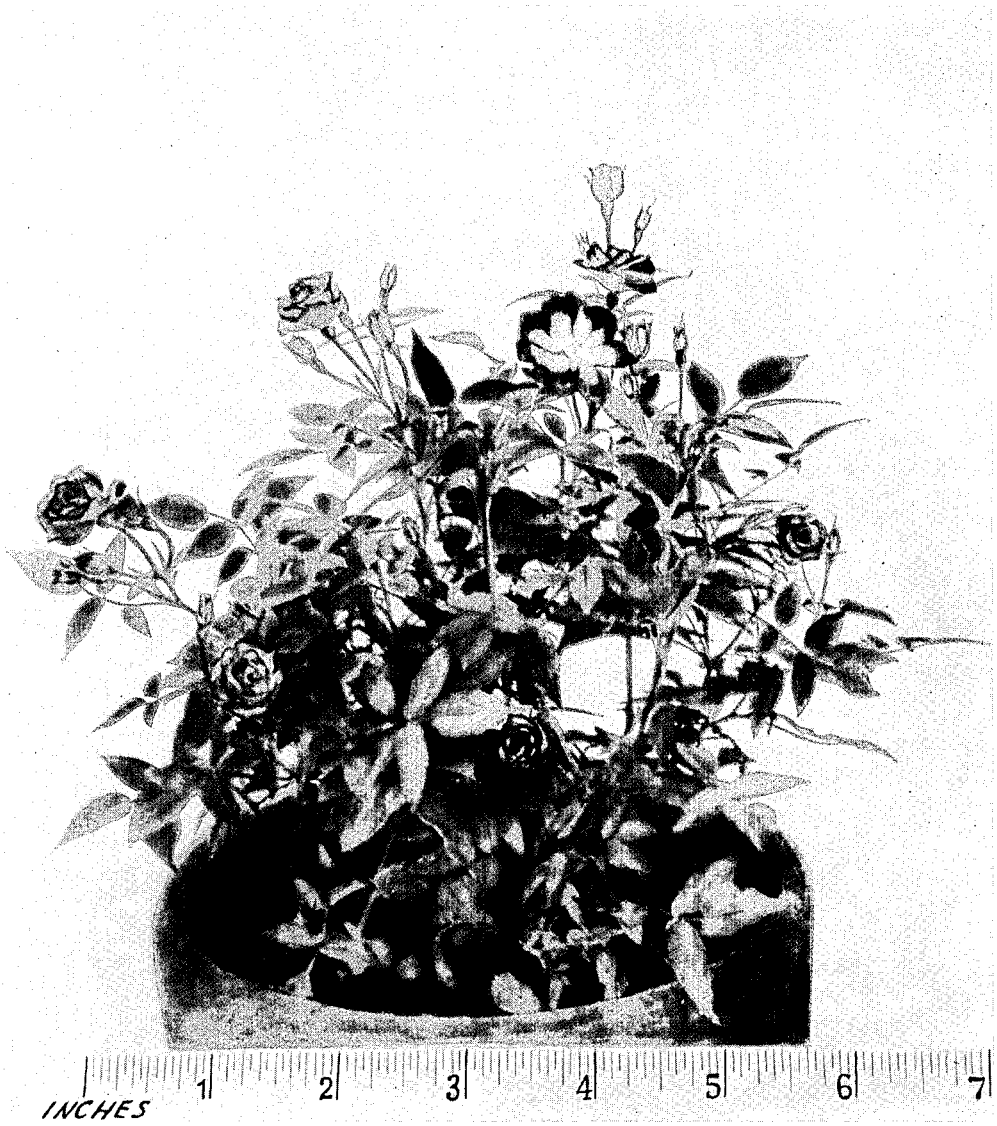
Inventor
John de Vink
By Robert Robb
Attorneys Patented Aug. 15, 1950

Plant Pat. 973

UNITED STATES PATENT OFFICE

973

ROSE PLANT

John de Vink, Boskoop, Netherlands, assignor to The Conard-Pyle Company, West Grove, Pa., a corporation of Pennsylvania Application August 5, 1949, Serial No. 108,761

1 Claim. (Cl. 47—61)

The present invention relates to a new and distinct variety of hardy rose plant of the miniature type, resulting from a cross of the polyantha rose "Eblouissant" and the miniature "Tom Thumb," both well known roses in commerce.

This new variety, unique among miniature roses, is characterized as to novelty in that it is a true miniature in growth and parts, but having a bud form that is a replica of the exhibition type of hybrid tea rose form, and a color of bloom of deep, true crimson, lasting throughout the life of the flower, something hitherto unknown in miniature roses that have as yet been introduced into commerce.

The drawing illustrates a specimen plant complete, in association with a scale to depict more clearly its miniature characteristic and also illustrating the flowers at different stages of development as well as the characteristic color, as nearly as this can be shown.

Asexual reproduction of this new variety shows that the foregoing characteristics come true to form and are established.

This new variety was asexually reproduced at West Grove, Pennsylvania, by cuttings.

The following is a detailed description of the new variety, reference to color being in accordance with Ridgway's Color Standards and Nomenclature where indicated and otherwise in accordance with the usual dictionary meaning.

Type: Hardy; dwarf; greenhouse; outdoor; seedling; for cut flowers and garden decoration.
Class: Miniature.
Breeding: Seedling.
*Seed parent.*—"Eblouissant" (unpatented).
*Pollen parent.*—"Tom Thumb" (Pl. Pat. #169).
Propagation: Holds its distinguishing characteristics through succeeding propagations.

*Flower*

Locality where grown: West Grove, Pennsylvania.
Flowers borne: Usually several to stem; in irregular cluster; on normal medium length stems.
Quantity of bloom: Free; outdoors and in greenhouse.
Continuity: Continuous.
Fragrance: Slight; tea.

Bud:
*Peduncle.*—Medium length; slender; erect; entirely smooth. Color—Lettuce Green, Plate V.
*Before calyx breaks.*—Size—Small. Form—ovoid; with foliaceous appendages on the surface of the bud; with slender foliaceous parts extending beyond the tip of the bud equal to one-fourth of its length.
*As calyx breaks.*—Color—Pomegranate Purple, Plate XII, with white at base.
*As first petal opens.*—Size—very small; about ⅜ inch in length. Form—ovoid. Color—Outside: Pomegranate Purple, Plate XII; Pale Green Yellow, Plate V, at base; inside: Oxblood Red, Plate I; Sulphur Yellow, Plate V, at base.
*Opening.*—Opens up well.
Bloom: Size, when fully open—very small; ¾ inch to 1 inch.
*Petalage.*—Semi-double; from 20 to 25 petals; arranged regularly.
*Form.*—Very cupped at first; becoming very open; petals remaining at first rolled outward; becoming later, at maturity, loosely rolled outward.
Petals: Thick; with inside velvety, and outside shiny and velvety toward tip.
*Shape.*—Outer—obovate with apex nearly flat. Intermediate—obovate with apex nearly flat. Inner—obovate.
*Color.*—Colors may be modified by a white streak down the midrib of the back of the petal; and by blackish shadings on edges of inner petal surface.

This description of a newly opened flower was made from a rose grown in a greenhouse in the month of April, at West Grove, Pennsylvania:

*Color.—Outer petal*—outside surface: light Pomegranate Purple, Plate XII; Pale Chalcedony Yellow, Plate XVII, at base; inside surface: light Oxblood Red to Oxblood Red, Plate I; white to Pale Chalcedony Yellow, Plate XVII, at base. *Intermediate petal*—outside surface: Pomegranate Purple, Plate XII; white to Pale Chalcedony Yellow, Plate XVII, at band; inside surface: light Pomegranate Purple, Plate XII, to Oxblood Red, Plate I, over most of petal surface; white to Pale Chalcedony Yellow, Plate XVII, at base. *Inner petal*—outside surface: dark Rose Red, Plate XII; white at base; inside surface: dark Rose Red, Plate XII, to Carmine, Plate I, over most of petal surface; white to light Sulphur Yellow, Plate V, at base.

This description was made from a rose that was open for three days in a greenhouse in the month of April at West Grove, Pennsylvania:

*Color.—Outer petal*—outside surface: Rose Red, to dark Rose Red, Plate XII; white at base; inside surface—light Pomegranate Purple, Plate XII, to Oxblood Red, Plate I, at edge of petal; white at base. *Inner petal*—outside surface: light Pomegranate Purple, Plate XII; white at base; inside surface: light Pomegranate Purple, Plate XII, over most of petal to Oxblood Red, Plate I, at apex; white at base.

*General color effect.*—Newly opened flower—Oxblood Red, Plate I; sometimes with shades of Pomegranate Purple, Plate XII. Three days open—white at center, shading to Rose Red, Plate XII, and to Oxblood Red, Plate I, over most of flower surface.

*Behavior.*—Drop off cleanly.

*Flower longevity.*—On bush in greenhouse—7 days in the month of April. Cut roses grown in greenhouse kept at living room temperatures, 3 to 4 days in April.

*Reproductive organs*

Stamens: Medium number; partly mixed with petaloids.

Filaments: Medium number; most with anthers; medium length; white.

Anthers: Open at various times; medium size; yellow; occasionally an anther fused with a petaloid.

Pollen: Moderate; gold.

Pistils: Medium number.

Styles: Almost even; medium length; medium heavy; columnar.

Stigma: Purplish white.

Ovaries: All enclosed in calyx.

Hips: Ovoid; moderately smooth; walls medium green.

Sepals: Permanent; medium length; spear-shaped.

Seeds: None discovered at time description was made.

*Plant*

Foliage:

*Leaves.*—Compound of five to seven leaflets; abundant; small; moderately heavy.

*Leaflets.*—Ovoid with apex acute; base obtuse; margin simply serrate.

*Color.—Mature*—upper surface: Grass Green, Plate VI; under surface: Deep Grape Green, Plate XLI. *Young*—upper surface: Javel Green, Plate V, with tinges of Pompeian Red, Plate XIII, at edges; under surface: Grape Green, Plate XLI, tinged with light Pompeian Red, Plate XIII.

*Rachis.*—Medium heavy; upper side grooved; under side thorny.

*Stipules.*—Short; narrow; medium length points, turning out at an angle of more than 45°.

*Disease.*—Resistant.

Growth:

*Habit.*—Bushy.

*Growth.*—Vigorous.

*Canes.*—Medium heavy.

*Main stems.*—Bright green. *Thorns*—several; slightly hooked downward; with oval base. *Prickles and hairs*—none.

*Branches.*—Bright green. *Thorns*—few; medium length; slightly hooked downward; with short oval base. *Prickles and hairs*—none.

*New shoots.*—Bright green. *Thorns*—several; medium length; slightly hooked downward; with short oval base. *Prickles and hairs*—none.

I claim:

A new and distinct variety of dwarf rose plant, characterized as to novelty by its unique miniature habit of growth; form of the bud; and the deep true crimson color of the flowers extending throughout the life of the flower, substantially as shown and described.

JOHN DE VINK.

No references cited.